United States Patent [19]

Pacifici et al.

[11] Patent Number: 5,039,481
[45] Date of Patent: Aug. 13, 1991

[54] ALIPHATIC POLYCARBOXYLIC ACIDS AS AIR PURIFICATION COMPOSITIONS

[75] Inventors: James G. Pacifici, Savannah, Ga.; Clel E. Lee, Mount Pleasant, S.C.

[73] Assignee: Clean Air, Inc., Savannah, Ga.

[21] Appl. No.: 530,500

[22] Filed: May 29, 1990

Related U.S. Application Data

[63] Continuation of Ser. No. 285,829, Dec. 16, 1988, abandoned.

[51] Int. Cl.$^5$ ................................................. A61L 9/00
[52] U.S. Cl. .................................................. 422/4; 422/5; 424/76.21; 424/76.6
[58] Field of Search ........................... 424/76.21; 422/4

[56] References Cited

U.S. PATENT DOCUMENTS

| | | | |
|---|---|---|---|
| 1,559,980 | 11/1925 | Perrott et al. | 423/237 |
| 1,586,327 | 5/1926 | Perrott et al. | 423/237 |
| 3,352,792 | 11/1967 | Clark et al. | 252/193 |
| 3,929,874 | 12/1975 | Beermann et al. | 260/534 M |
| 3,964,486 | 6/1976 | Blaney | 424/414 X |
| 3,989,498 | 11/1976 | Cox | 424/76.6 |
| 4,070,300 | 1/1978 | Moroni et al. | 252/190 |
| 4,230,478 | 10/1980 | Zumbrunn | 71/21 |
| 4,405,354 | 9/1983 | Thomas, II et al. | 119/1 |
| 4,638,763 | 1/1987 | Greenberg | 119/1 |
| 4,816,220 | 3/1989 | Roychowdhury | 424/76.6 |

FOREIGN PATENT DOCUMENTS 0051755 4/1977 Japan.
0056176 5/1978 Japan.

OTHER PUBLICATIONS

Chemical Abstracts, vol. 84, p. 304 (1976), 84: 35371h.
Chemical Abstracts, vol. 84, p. 304 (1976), 84: 35372j.
Chemical Abstracts, vol. 42, (1948).

Primary Examiner—Jill Johnston
Attorney, Agent, or Firm—Pennie & Edmonds

[57] ABSTRACT

A method for reducing the amount of ammonia released into the air in a livestock enclosure by the decomposition of livestock excrement or urine by applying to areas of the enclosure where livestock excrement or urine accumulates an ammonia scavenging composition that contains an aliphatic polycarboxylic acid in an amount sufficient to scavenge a portion of the ammonia which is generated due to the decomposition of the livestock excrement or urine, thereby reducing the amount of ammonia released into the air within the enclosure.

28 Claims, No Drawings

ALIPHATIC POLYCARBOXYLIC ACIDS AS AIR PURIFICATION COMPOSITIONS

This is a continuation of application Ser. No. 07/285,829, filed Dec. 16, 1988, now abandoned.

TECHNICAL FIELD

This invention relates to the novel use of aliphatic polycarboxylic acids as air purification compositions, and particularly for controlling the ammonia levels generated in livestock areas. Ammonia produced via anaerobic breakdown of excrement and urine is efficiently scavenged when livestock areas are treated with such compositions according to the inventions.

BACKGROUND

Ammonia is one of the major gases produced by anaerobic breakdown of excrement and urine in livestock areas. Its generation and control is a major problem associated with confined livestock operations.

Excessively high ammonia levels in the air are well known to be associated with both swine and poultry operations and have been of major concern to these industries. High ammonia levels have a detrimental effect on the health of hogs causing respiratory tract problems, pneumonia and inflammation of the nasal mucosa. Blindness and significant death loss in both poultry broiler and layer operations has been associated with high levels of ammonia produced in these areas. In addition to the identified health problems associated with high levels of ammonia, the average daily weight gain of hogs is also affected. Studies have shown that levels of ammonia in the air exceeding 25 ppm reduce the average daily weight gain of the animals by approximately 12%. Conventional methods of reducing the ammonia levels in livestock operation such as forced air systems are not always effective because they do not reduce the level of ammonia generated which ultimately diffuses into the air. These systems strive only to remove the toxic gases by displacement of the contaminated air. Enclosed areas, such as pig nurseries, are particularly vulnerable to inefficient removal of contaminated air during cold weather conditions.

One solution to this problem is presented in U.S. Pat. No. 3,352,792 wherein a dry powder mixture of borax and magnesium carbonate is used as a litter material to absorb uric wastes discharged from the animals.

It is also known to use solutions of alkylbenzenesulfonic acid and boric acid in water as a deordorant from human waste (Chemical Abstracts, 84, 35371 h, 1976) as well as to spray solutions of 3-5% glacial acetic acid on waste materials to reduce the odor of ammonia (Chemical Abstracts 84, 35372 j 1976).

A filter material for removing odors from air is disclosed in U.S. Pat. No. 4,070,300. This filter material may include, among many suitable chemisorbent materials, organic polycarboxylic or monocarboxylic acids. Other references also discuss the removal of ammonia from air by filtering, see e.g., U.S. Pat. Nos. 1,586,327 and 1,559,980.

None of these references, however, achieve the results which are attainable by the process of the present invention. Accordingly, the invention is able to overcome the disadvantages associated with the processes currently available and described in the prior art by providing highly efficient compositions for direct application to waste environments.

SUMMARY OF THE INVENTION

The present invention provides compositions which are particularly effective for scavenging ammonia generated in animal waste environments, and for retarding the rate of ammonia generated in such waste environments. In particular, the inventive compositions have been found to be effective at providing long-term scavenging and retarding capability.

It has been found that aliphatic polycarboxylic acids (the term polycarboxylic acid is used to indicate multifunctional carboxyl groups) are unusually effective at reducing the ammonia levels generated in livestock operations. These acids show unexpected behavior because they provide long term scavenging activity when applied in the manner disclosed by this invention. In comparison, aliphatic monocarboxylic acids have been fount to not be effective for controlling ammonia levels to the required levels, e.g., 20 ppm or less.

DETAILED DESCRIPTION OF THE INVENTION

The aliphatic polycarboxylic acids useful in the invention have the following general formulas:

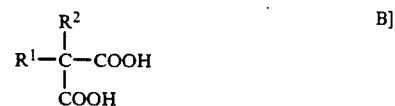

wherein $R^1$ and $R^2$, which can be the same or different, are H or a lower alkyl moeity such as methyl, ethyl, or propyl, or an integral part of a cyclic system of six carbon atoms or less.

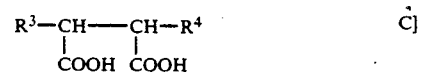

wherein $R^3$ and $R^4$, which can be the same or different, are H, a lower alkyl, or hydroxyl moeity; or an integral part of a cyclic system of six carbons or less.

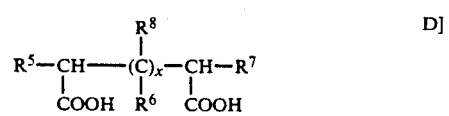

wherein $R^5$ and $R^7$, which can be the same or different, are H, a lower alkyl moeity, or an integral part of a cyclic system of six carbons or less; $R^6$ can be H, a hydroxyl or carboxyl moeity; and $R^8$ can be H, or a lower alkyl moeity; with $x=1$ or 2.

wherein n is 10 to 2000 and defines the number of repeating units in the polymer chain.

Typical aliphatic polycarboxylic acids which are useful in this invention are oxalic acid, malonic acid, succinic acid, malic acid, citric acid, 1,2-cyclohexane dicarboxylic acid, 1,3-cyclohexane dicarboxylic acid, 1,4-cyclohexane dicarboxylic acid, 1,1-cyclobutane dicarboxylic acid, 1,2-cyclopentane dicarboxylic acid, and poly(acrylic acid). Accordingly, in a more preferred embodiment of this invention these acids are used from 0.1 to 25 percent by weight. More advantageous acid concentrations range from 1 to 15 and most preferably 5 to 10 percent by weight of the compositions.

These acids can be used alone or admixed with dispersing or solubilizing agents. Typical dispersing agents are salts such as sodium chloride, aluminum sulfate and sodium sulfate. The dispersing agents may be used in an amount of between 0.1 and 50 percent by weight of the overall composition, preferably 5 to 10 percent. Solubilizing agents which are particularly effective are water and low molecular weight glycols such as ethylene glycol, propylene glycol, diethylene glycol, and triethylene glycol. These solubilizing agents can be used in an amount of between 0.1 and 25 percent by weight of the overall composition, preferably 1 to 5 percent.

Other ingredients such as fragrances can also be used in combination with the formulation to be applied to the livestock area. Fragrances such as lemon, pine, cherry, baby powder and orange are useful in a concentration of between 0.1 and 5 percent by weight of the overall composition.

The aliphatic polycarboxylic acid compositions can be applied in a variety of ways depending on the specific type of livestock operation. For example, a composition can be added directly to a flush system commonly used in hog operations such as farrowing houses, nurseries and feed-out buildings.

For operations where flush systems are not employed, the compositions in dry form can be used on the floors prior to wash down with water. The most efficient method of application is to spray a liquid composition via a mechanical spray system which operates on an electrical timer. Such a system enables more efficient control of the amount of material needed for optimum ammonia scavenging.

Dry compositions can be obtained by mixing or spraying these acids onto solid absorbent materials such as those commonly used in poultry broiler operations, e.g. sawdust and/or rice hulls.

EXAMPLES

This invention will be further illustrated by the following examples, although it will be understood that these examples are included merely for purpose of illustration and are not intended to limit the scope of the invention.

EXAMPLES 1–8

Treatment of Pig Nurseries

Experimental nurseries containing 75–100 pigs, each having a weight range of 20–50 pounds and equipped with 200 gallon flush tanks were utilized in this experiment. These nurseries had concrete floors three feet below the pens which were washed via the flush tank every 12 hours. The compositions described in the table were evaluated for effectiveness in the following way:

a. Compositions were added to each flush tank prior to the designated flush time.

b. Initial ammonia levels were measured for each nursery using a Gastec Model 800 ammonia testing equipment (SEI Ref. No. GDSGT05.) This was accomplished by taking ammonia readings at six different locations in the building approximately 5 feet above the floor. The average value of the six readings was recorded.

c. Flush tanks were discharged and after one hour ammonia levels were taken in the same manner as Step B.

d. Ammonia levels were monitored for 10 hours after the initial flush.

e. Subsequent flush operations used water which did not contain acid.

f. After a total of 48 hours (i.e., 3 further flushes at 12 hour intervals) the ammonia levels were again determined.

Results are illustrated in Table 1. Note that the compositions of the invention (Examples 5–8) provide a substantial improvement over the control (Example I) and mono carboxylic acids (Examples 2–4).

TABLE 1

| | TREATMENT OF PIG NURSERIES | | | | | |
|---|---|---|---|---|---|---|
| EXAMPLE NO. | COMPOSITION* | AMT. (Lbs.) | Ammonia level** (ppm) | | | |
| | | | INITIAL | 1 HR | 10 HRS | 48 HRS |
| 1 | None | 5 | 86 | 90 | 75 | 87 |
| 2 | Acetic Acid | 5 | 74 | 67 | 70 | 70 |
| 3 | Propionic Acid | 5 | 82 | 80 | 75 | 86 |
| 4 | Sulfamic Acid | 5 | 82 | 40 | 50 | 84 |
| 5 | Oxalic Acid | 2 | 88 | <5 | <5 | 10 |
| 6 | Citric Acid | 2 | 79 | 6 | <5 | 10 |
| 7 | Poly (acrylic acid) Mol. wt. 2000 | 2 | 85 | <5 | 10 | 6 |
| 8 | Oxalic Acid | 5 | 80 | <5 | <5 | <5 |

*Amount of product added to 200 gallon flush tank.
**Average value of six determinations.

EXAMPLE 9

Treatment of Farrowing House

A farrowing house 60 feet long and having 12 crates above a concrete floor equipped with a flush system (500 gallon capacity) each crate containing a sow (average weight 400 pounds) and 7–9 piglets per sow (2–10 pounds each) was treated with oxalic acid as follows. 5 pounds of oxalic acid was added to the flush tank. The initial ammonia level was measured and found to be 28 ppm. After flushing, the level dropped to <5 ppm and maintained this level for three days.

EXAMPLES 10–15

Effective Ammonia Scavenging Compositions

Each of the following compositions is effective in reducing ammonia in farrowing houses to below 5 ppm. These farrowing houses contained 30 to 50 sows and were equipped with 300 gallon flush tanks. The compositions were added to water to provide a 0.2 percent by weight acid solution.

| Example | Ingredients | Weight Percent |
|---|---|---|
| 10 | Oxalic Acid | 5 |
| | Sodium Chloride | 95 |
| 11 | Oxalic Acid | 5 |
| | Sodium Sulfate | 95 |
| 12 | Oxalic Acid | 10 |
| | Aluminum Sulfate | 5 |
| | Sodium Chloride | 85 |
| 13 | Oxalic Acid | 10 |
| | Citric Acid | 10 |
| | Sodium Chloride | 80 |
| 14 | Oxalic Acid | 10 |
| | Sodium Chloride | 85 |
| | Lemon Fragrance | 5 |
| 15 | Oxalic Acid | 10 |
| | Sodium Chloride | 70 |
| | Sodium Sulfate | 10 |
| | Aluminum Sulfate | 10 |

EXAMPLES 16–22

Elimination of Ammonia from Poultry Litter

Poultry litter from a freshly emptied broiler house which contained 20,000 broiler chickens was collected from several random locations in the house. The litter was combined and blended to provide samples for ammonia production and elimination studies. The samples were placed in one square foot containers to a depth of four inches. The height of the containers was twelve inches and ammonia levels were measured at a height of six inches above the litter sample. This was accomplished employing A-15 Ammonia Sensitive Indicator Strips (American Gas and Chemical Co., Ltd). The time required in hours to produce an ammonia level of 100 ppm was determined; this was determined for control (untreated) samples of litter and samples treated with the following compositions.

| Example | Composition | Weight Percent |
|---|---|---|
| 16 | Oxalic Acid | 100 |
| 17 | Citric Acid | 100 |
| 18 | Oxalic Acid | 50 |
| | Citric Acid | 50 |
| 19 | Oxalic Acid | 90 |
| | Boric Acid | 10 |
| 20 | Oxalic Acid | 45 |
| | Citric Acid | 45 |
| | Boric Acid | 10 |
| 21 | Poly (acrylic acid) | 100 |
| 22 | Oxalic Acid | 50 |
| | Poly (acrylic acid) | 50 |

These compositions were added to water to produce an aqueous solution containing approximately 10 percent by weight solids. The aqueous solutions were sprayed on the sample of litter. Each composition was sprayed on three samples at three different concentration levels. The results of these experiments are listed in Table II.

TABLE II
REDUCTION OF AMMONIA IN POULTRY LITTER

| Example[a] | Grams/Sq. Ft. | Time (Hours)[b] |
|---|---|---|
| Control | N/A | 0.03 |
| 16 | 1 | 36 |
| | 3 | 240 |
| | 8 | 460 |
| 17 | 1 | 18 |

TABLE II-continued
REDUCTION OF AMMONIA IN POULTRY LITTER

| Example[a] | Grams/Sq. Ft. | Time (Hours)[b] |
|---|---|---|
| | 3 | 160 |
| | 8 | 300 |
| 18 | 1 | 40 |
| | 3 | 300 |
| | 8 | 520 |
| 19 | 1 | 70 |
| | 3 | 250 |
| | 8 | 500 |
| 20 | 1 | 100 |
| | 3 | 360 |
| | 8 | 620 |
| 21 | 1 | 15 |
| | 3 | 110 |
| | 8 | 380 |
| 22 | 1 | 40 |
| | 3 | 200 |
| | 8 | 390 |

EXAMPLE 23

Typical Procedure for Treatment of Broiler Houses with Ammonia Scavenging Compositions A broiler house with 12,000 sq. ft. of floor which had been cleaned out, tilled and covered with wood chips was sprayed with 150 gallons of an aqueous solution of ammonia scavenging composition. The composition was composed of 45 pounds of oxalic acid, 45 pounds of citric acid and 10 pounds of boric acid. The initial ammonia level in the house (with curtains up) was 500 ppm and after uniformly spraying the solution, the ammonia level dropped to less than 1 ppm.

From the preceding examples it can be seen that the periodic application of a polycarboxylic acid composition to the floor or other areas where livestock excrement and urine accumulate enables a highly effective control of ammonia vapor generated from the decomposition of such excrement and urine. When a periodic water flush is utilized, as in Examples 5–8, the acid solution only needs to be utilized once every four to six days to obtain the desired ammonia control, despite that a water flush is applied approximately every twelve hours. This is completely unexpected compared to the poor results obtained with the monocarboxylic acids of Examples 2–4. Also, it is possible to utilize dry acid-containing compositions with similar results.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method for reducing the amount of ammonia released into the air by the decomposition of livestock excrement or urine which comprises contacting livestock excrement or urine with an ammonia scavenging composition that contains an aliphatic polycarboxylic acid of oxalic acid, 1,2-cyclohexane dicarboxylic acid, 1,3-cyclohexane dicarboxylic acid, 1,4-cyclohexane dicarboxylic acid, 1,1-cyclobutane dicarboxylic acid, 1,2-cyclopentane dicarboxylic acid or polyacrylic acid in an amount sufficient to scavenge a portion of the ammonia which is generated by decomposition of said livestock excrement or urine.

2. The method of claim 1 wherein the composition further includes a solubilizing agent and the solubilizing agent is water or a glycol.

3. The method of claim 1 wherein the composition further includes a dispersing agent.

4. The method of claim 3 wherein the dispersing agent is a halide or sulfate salt.

5. The method of claim 1 wherein the composition further includes a fragrance.

6. The method of claim 1 wherein the composition further includes an absorbent.

7. The method of claim 6 wherein the absorbent is sawdust or rice hulls.

8. The method of claim 1 wherein the acid is oxalic acid.

9. A method for reducing the amount of ammonia released into the air by the decomposition of livestock excrement or urine which comprises contacting livestock excrement or urine with an ammonia scavenging composition that contains an aliphatic polycarboxylic acid of oxalic acid, 1,2-cyclohexane dicarboxylic acid, 1,3-cyclohexane dicarboxylic acid, 1,4-cyclohexane dicarboxylic acid, 1,1-cyclobutane dicarboxylic acid, 1,2-cyclopentane dicarboxylic acid or polyacrylic acid and a solubilizing agent, said acid added in an amount sufficient to scavenge a portion of the ammonia which is generated by decomposition of said livestock excrement or urine.

10. The method of claim 9 wherein the solution is used to flush areas where said excrement or urine accumulates wherein the acid is present in a concentration of between 0.1 and 25 percent by weight of the solution.

11. The method of claim 9 wherein the solubilizing agent is water and wherein the acid is present in a concentration of between 1 and 15 percent by weight of the solution.

12. The method of claim 9 wherein the solution further includes a dispersing agent in a concentration of between 0.1 and 50% by weight of the solution.

13. The method of claim 9 wherein the acid is oxalic acid and wherein the solubilizing agent is water or a glycol.

14. A method for reducing the amount of ammonia released into the air in a livestock enclosure by the decomposition of livestock excrement or urine which comprises applying to areas of the enclosure where livestock excrement or urine accumulates an ammonia scavenging composition that contains an aliphatic polycarboxylic acid of oxalic acid, 1,2-cyclohexane dicarboxylic acid, 1,3-cyclohexane dicarboxylic acid, 1,4-cyclohexane dicarboxylic acid, 1,1-cyclobutane dicarboxylic acid, 1,2-cyclopentane dicarboxylic acid or polyacrylic acid in an amount sufficient to scavenge a portion of the ammonia which is generated due to the decomposition of the livestock excrement or urine.

15. The method of claim 14 wherein the absorbent is sawdust or rice hulls.

16. The method of claim 14 wherein the composition further includes a solubilizing agent and the solubilizing agent is water and wherein the acid is present in a concentration of between 0.1 and 15% by weight of the solution.

17. The method of claim 16 wherein the composition further includes a dispersing agent in a concentration of between 5 and 10% by weight of the solution.

18. The method of claim 14 wherein the acid is oxalic acid.

19. A method for reducing the amount of ammonia released into the air by the decomposition of organic waste material which comprises contacting organic waste with an ammonia scavenging composition containing oxalic acid in an amount sufficient to scavenge a portion of the ammonia generated by such decomposition.

20. A method for reducing the amount of ammonia released into the air by the decomposition of livestock excrement or urine which comprises contacting livestock excrement or urine with an ammonia scavenging composition that contains an aliphatic polycarboxylic acid in combination with boric acid, said combination being present in an amount sufficient to scavenge a portion of the ammonia generated by such decomposition.

21. The method of claim 20 wherein the aliphatic polycarboxylic acid is oxalic acid, malonic acid, succinic acid, malic acid, citric acid, 1,2-cyclohexane dicarboxylic acid, 1,3-cyclohexane dicarboxylic acid, 1,4-cyclohexane dicarboxylic acid, 1,1-cyclobutane dicarboxylic acid, 1,2-cyclopentane dicarboxylic acid, or poly(acrylic acid).

22. The method of claim 20 wherein the composition further includes a solubilizing agent.

23. The method of claim 22 wherein the solubilizing agent is water or a glycol.

24. The method of claim 20 wherein the composition further includes a dispersing agent.

25. The method of claim 24 wherein the dispersing agent is a halide or sulfate salt.

26. The method of claim 20 wherein the composition further includes a fragrance.

27. The method of claim 26 wherein the composition further includes an absorbent.

28. The method of claim 27 wherein the absorbent is sawdust or rice hulls.

* * * * *